US 6,673,108 B2
Jan. 6, 2004

(12) United States Patent
Zilla et al.

(54) TRANSMURAL CONCENTRIC MULTILAYER INGROWTH MATRIX WITHIN WELL-DEFINED POROSITY

(75) Inventors: Peter Paul Zilla, Camps Bay (ZA); Deon Bezuidenhout, Stellenbosch (ZA); Theresa Yvonne Dower, Hout Bay (ZA)

(73) Assignee: Medtronic, Inc, Minneapolis, MN (US)

( * ) Notice: Subject to any disclaimer, the term of this patent is extended or adjusted under 35 U.S.C. 154(b) by 0 days.

(21) Appl. No.: 10/142,957

(22) Filed: May 10, 2002

(65) Prior Publication Data

US 2002/0151968 A1 Oct. 17, 2002

Related U.S. Application Data

(63) Continuation of application No. 09/434,069, filed on Nov. 5, 1999, now Pat. No. 6,554,857.
(60) Provisional application No. 60/144,703, filed on Jul. 20, 1999.

(51) Int. Cl.⁷ .................................................. A61F 2/06
(52) U.S. Cl. ....................................... 623/1.4; 623/1.44
(58) Field of Search ............................... 623/1.28, 1.29, 623/1.32, 1.33, 139–1.54, 2.12, 2.42, 1.4, 1.44, 23.74, 23.76; 435/395, 398

(56) References Cited

U.S. PATENT DOCUMENTS

| | | | |
|---|---|---|---|
| 4,286,341 A | 9/1981 | Greer et al. | 3/1.4 |
| 4,441,215 A | 4/1984 | Kaster | 3/1.4 |
| 4,552,707 A | 11/1985 | How | 264/24 |

(List continued on next page.)

FOREIGN PATENT DOCUMENTS

| | | | | |
|---|---|---|---|---|
| EP | 560279 A1 | 9/1993 | | A61L/27/00 |
| EP | 562079 B1 | 9/1993 | | A61L/27/00 |
| EP | 0815806 A2 | 1/1998 | | A61F/2/06 |
| WO | WO 90/06094 | 6/1990 | | A61F/2/06 |
| WO | WO 97/15242 | 5/1997 | | A61F/2/02 |
| WO | WO 9717254 | 12/1997 | | A61B/19/00 |

OTHER PUBLICATIONS

Annis et al.,, Trans. Am. Soc. Artif. Intern Organs, vol. XXIV, 1978, pp 209–214.
Berkowitz, Henry D., et al.,, Amer Soc Artif Int Organs, vol XVIII, 1972, pp 25–29.
Berkowitz, Henry D., M.D., et al., Surgery, vol. 72, No. 6, Dec 1972, pp 888–896.
Edwards, Alan et al., Jrnl of Biiomaterials Applications, vol 10, Oct 1995, pp 171–187.
Hess, F., J. Cardiovascular Surgery, 24, 1983.
Hess, F., et al.,, Biomaterials, vol 13, No., 10, 1992, pp 657–663.
Hess, F., M.D. et al.,, Jrnl of Cardio Surg, vol 22, 1992, pp 358–365.
Hiratzka, Loren, F., M.D., et al., Arch Surg, vol 114, Jun. 1979, pp 698–702.

(List continued on next page.)

*Primary Examiner*—Corrine McDermott
*Assistant Examiner*—Hieu Phan
(74) *Attorney, Agent, or Firm*—Kenneth J. Collier

(57) ABSTRACT

A multilayer ingrowth matrix is constructed within well-defined porosity of a prosthetic material. The matrix consists of either proteinaceous or synthetic layers or gradients, or a combination of proteinaceous and synthetic layers or gradients. Each layer within the matrix is designed to achieve a specific function, such as facilitation of ingrowth of a particular cell type or release of a particular growth factor. The well-defined porosity is in the form of either helically oriented, interconnected transmural ingrowth channels, or a porous wall structure containing uniformly shaped pores (i.e. voids) in a very narrow size range, or a combination of channels and pores. This invention allows for uninterrupted ingrowth of connective tissue into walls of a synthetic graft prosthesis made from the prosthetic material. Furthermore, this invention can produce small diameter prostheses having an internal diameter of 6 mm or less.

15 Claims, 3 Drawing Sheets

U.S. PATENT DOCUMENTS

| | | | |
|---|---|---|---|
| 4,605,406 A | 8/1986 | Cahalan | 623/1 |
| 4,657,544 A | 4/1987 | Pinchuk | 623/1 |
| 4,725,273 A | 2/1988 | Kira | 623/1 |
| 4,743,252 A | 5/1988 | Martin, Jr. et al. | 623/1 |
| 4,784,659 A | 11/1988 | Fleckenstein et al. | 623/1 |
| 4,842,575 A | 6/1989 | Hoffman, Jr. et al. | 600/36 |
| 4,873,308 A | 10/1989 | Coury et al. | 528/75 |
| 4,921,495 A | 5/1990 | Kira | 623/1 |
| 4,941,870 A | 7/1990 | Okada et al. | 600/36 |
| 5,024,671 A | 6/1991 | Tu et al. | 623/1 |
| 5,037,377 A | 8/1991 | Alonso | 600/36 |
| 5,108,424 A | 4/1992 | Hoffman, Jr. et al. | 623/1 |
| 5,132,066 A | 7/1992 | Charlesworth et al. | 264/184 |
| 5,197,977 A | 3/1993 | Hoffman, Jr. et al. | 623/1 |
| 5,415,619 A | 5/1995 | Lee et al. | 600/36 |
| 5,455,100 A * | 10/1995 | White | 428/131 |
| 5,549,664 A | 8/1996 | Hirata et al. | 623/1 |
| 5,584,875 A | 12/1996 | Duhamel et al. | 623/1 |
| 5,628,781 A | 5/1997 | Williams et al. | 623/1 |
| 5,709,934 A | 1/1998 | Bell | 428/305.5 |
| 5,770,417 A | 6/1998 | Vacanti et al. | 435/180 |
| 5,807,406 A | 9/1998 | Brauker et al. | 623/11 |
| 6,240,616 B1 * | 6/2001 | Yan | 29/527.2 |
| 6,273,913 B1 * | 8/2001 | Wright et al. | 623/1.42 |
| 6,379,381 B1 * | 4/2002 | Hossainy et al. | 623/1.42 |
| 6,432,131 B1 * | 8/2002 | Ravenscroft | 623/1.13 |

OTHER PUBLICATIONS

Ivens, C.L., et al., Trans Am Soc Artif Intern Organs, vol XXX, 1984, pp 587–590.

Leidner, Jacob et al., Jrnl of Biomedical materials Research, vol 17, pp 229–247.

Lyman, D.J., et al., Trans Am Soc Artif Intern Organs, vol XXIII, 1977, pp 253–261.

Murabayashi, S. et al., Trans Am Soc Artif Intern Organs, vol XXXI, 1985, pp 50–55.

Pollock, E., et al., Trans Am Soc Artif Intern Organs, vol XXVII, 1981, pp 405–409.

Uchida, Naoki et al., Jrnl of Biomedical Materials Research, vol 27, 1993, pp 1269–1279.

Weber, Jon N., et al., Science, vol. 176, May 26, 1972, pp 922–924.

White, Rodney, A., et al., Surgery, vol 79, No. 2, Feb 1976, pp 229–232.

Williams, Stuart K., et al., Jrnl of Biomedical Materials Research, vol 26, pp 103–117.

Wilson, G.J., Trans Am Soc Artif Intern Organs, vol XXIX, 1983, pp 260–268.

* cited by examiner

TRANSMURAL CONCENTRIC MULTILAYER INGROWTH MATRIX WITHIN WELL-DEFINED POROSITY

This appln is a con't of Ser. No. 09/434,069 filed Nov. 5, 1999 U.S. Pat. No. 6,554,857 and claims benefit of Prov. No. 60/144,703 filed Jul. 20, 1999.

FIELD OF THE INVENTION

This invention is directed to a prosthetic material having a multilayer ingrowth matrix within well-defined pores and/or channels within the material. Each layer of the matrix is either proteinaceous or synthetic, or a combination of proteinaceous and synthetic materials. Each layer of the matrix is designed to perform a specific function, such as facilitation of ingrowth of a particular cell type or release of a particular growth factor. Instead of distinct layers, the matrix can comprise concentration gradients of the same materials. A suitable application of the prosthetic material is a vascular graft.

BACKGROUND OF THE INVENTION

Vascular disease in small to medium diameter arteries adversely affects arterial wall structure. As a result, blood flow through the vessel is hindered either by total occlusion or, in the opposite extreme, an acute over dilation of the vessel (aneurysm). Such indications usually require reconstructive or bypass surgery. The most successful replacements at present are autologous grafts (arteries and veins taken from the host), but often these are too diseased or unsuitable for use as an implant. There is thus a great need for the development of a reliable, fully integrated, vascular prosthesis.

Over the last 40 years, considerable progress has been made in the development of arterial prostheses. The modern era of vascular surgery began in the early 1950's, 40 years after Carrel and Gutherie (1906) demonstrated that autologous veins could be used to replace arteries. With the advent of antibiotics and anticoagulants in ancillary medicine, the development of vascular prostheses prospered. The reversed saphenous vein was soon considered the best artery replacement and was used successfully in femoral artery replacement by Kunlin in 1949. However, the need for a smaller prosthesis led to further research by Gross and associates involving homografts using sterilized tissue. Although early results were encouraging, the long-term results were still unsatisfactory, with the grafts often failing due to thrombosis and aneurysm.

While pioneers such as Gross et al. (1948) continued to work on hetero- and homografts, Voorhees made an important observation in 1952 that changed the direction of vascular prosthetic development. After discovering that cells grew on silk thread exposed to blood, he showed the effectiveness of synthetic textile or fabric tubes as arterial replacements. A new era of vascular surgery began and the search for the most suitable material and optimal structure for a textile graft began. Experiments, even recently, have investigated factors such as knitted or woven textiles, large or small pores, different surface finishes and crimping and external reinforcing.

Presently, the materials used for vascular implants are tanned natural vessels, textile tubes made from woven or knitted Dacron, or tubes made from expanded polytetrafluoroethylene (e-PTFE). These grafts are successful for large diameter artery replacement where there is a high blood flow rate; but they have a much lower success rate in arteries with a diameter less than 6 mm. These conventional prosthetic vascular grafts do not permit unrestricted vessel ingrowth from the surrounding tissue due mostly to ingrowth spaces that are either too narrow or discontinuous. All of the present grafts eventually fail by occlusion due to thrombosis (fibrous tissue build up), or intimal hyperplasia (exuberant muscle growth at the interface between artery and graft).

Factors such as the thrombogenic nature of the graft material, surface roughness, the mechanical and haemodynamic properties of the graft and the condition of the host artery are known to influence the success of the graft. Although the reasons for failure are not fully understood, it is largely agreed that compliance mismatch between artery and graft is the predominant issue surrounding the failure of small diameter prostheses. Discontinuity in mechanical properties between the graft and artery alters the blood flow resulting in a fibrous tissue build-up leading to the complete occlusion and hence failure of the graft.

Autologous grafts, such as the saphenous vein and the internal mammary artery are still considered the best grafts for the reconstruction of small peripheral arteries, but these are often too diseased or unsuitable for use as a graft. None of the present textile grafts (e-PTFE and Dacron) have proved successful for long periods. Many approaches to graft production have been developed in an effort to create a porous polyurethane artery graft. Indeed, it has been shown that it is possible to create an initially compliant porous graft. However, the long-term success of such grafts remains to be proven. It has become apparent that the current methods of graft construction are ineffectual and a new approach is necessary.

It is evident that the present small diameter grafts do not provide an acceptable long-term patency. Although the causes for failure are not immediately clear, it is apparent that none of the previous prostheses have the same structure as an artery or behave mechanically as an artery does. The focus of graft "healing" has traditionally been to achieve endothelialization. Until now, research has concentrated on developing a prosthetic material which facilitates transmural angiogenesis. However, "healing" appears to encompass more than endothelialization and, therefore, the focus should extend beyond the stimulation of only angiogenesis. Full integration of a vascular prosthesis involves not only endothelial cell migration and proliferation leading to a functional endothelium, but also the establishment of a functional neo-media. This would require the ingrowth of additional cell types, specifically smooth muscle cells. Furthermore, current designs of prosthetic material typically prioritize ingrowth of one cell type over another.

SUMMARY OF THE INVENTION

The present invention is directed to a prosthetic material. More particularly, the material comprises a multilayer ingrowth matrix within well-defined porosity. The matrix consists of either proteinaceous or synthetic layers or a combination of proteinaceous and synthetic layers. Each layer is designed to achieve a specific function, such that angiogenesis/endothelial ingrowth can be stimulated within one layer while smooth muscle cell ingrowth is simultaneously stimulated in a second layer, for example.

The well-defined porosity is in the form of either helically oriented, interconnected transmural ingrowth channels, or a porous wall structure containing uniformly shaped pores (i.e. voids) in a very narrow size range, or a combination of channels and pores. This invention allows for uninterrupted ingrowth of connective tissue into walls of the synthetic graft prosthesis. The problem of compliance mismatch encountered with conventional grafts is also addressed by matching mechanical properties of the graft with mechanical properties of a host vessel. These mechanical properties include smoothness, elasticity and structural integrity.

With the foregoing in mind, it is a feature and advantage of the invention to provide a prosthetic material having a multilayer ingrowth matrix within well-defined porosity.

It is another feature and advantage of the invention to provide a prosthetic material having a multilayer ingrowth matrix wherein each layer is designed to perform a specific function.

It is a further feature and advantage of the invention to provide a prosthetic material that has a surface pacifying coating and ingrowth layers within well-defined porosity for the ingrowth of specific cells, including smooth muscle cells and endothelial cells.

DETAILED DESCRIPTION OF THE PRESENTLY PREFERRED EMBODIMENTS

This invention is directed to an improved prosthetic material having a transmural scaffold (i.e. from the lumenal surface through to the adventitial surface) with a multilayer ingrowth matrix located within either a network of interconnected, helically oriented channels or within uniformly shaped pores (i.e. voids) within the scaffold, or a combination of both channels and pores. Each layer, or gradient, of the matrix is designed to perform a specific function, for example, angiogenesis/endothelial ingrowth can be stimulated within one layer while smooth muscle cell ingrowth is simultaneously stimulated in a second layer. Smooth muscle cell ingrowth generates contractility and can alleviate issues of mismatch of compliance. Further examples of specific functions that can be performed by each layer include facilitation of ingrowth of a particular cell type or release of a particular growth factor.

Figure 1:
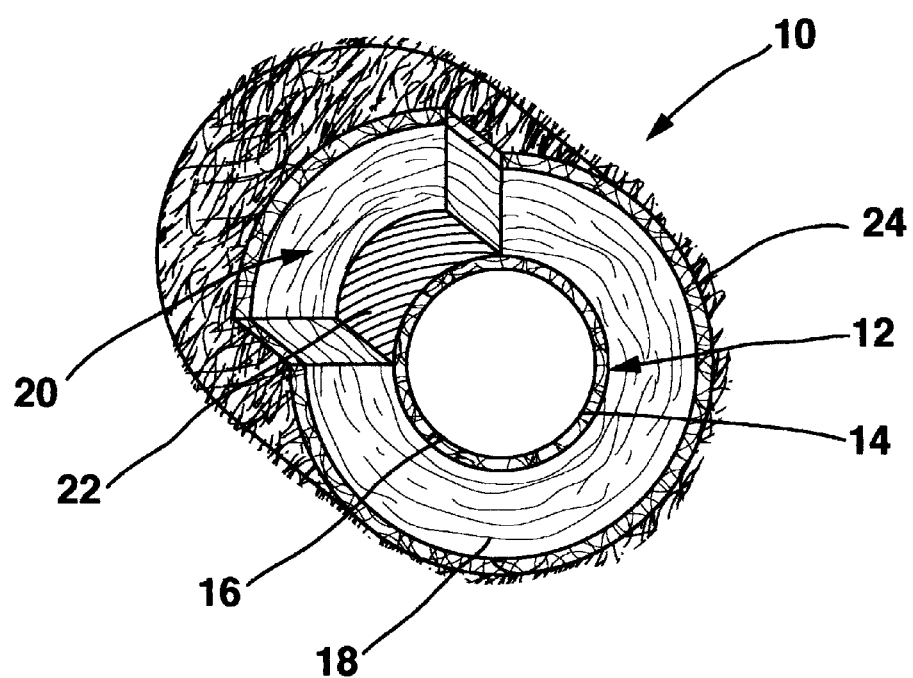
FIG. 1 is an enlargement of a cross-sectional view of a sliced section of a "typical" artery.

In order to promote ingrowth of connective tissue, it is important that mechanical properties of the graft (especially smoothness, elasticity and structural integrity) are closely matched with mechanical properties of a host vessel, thereby overcoming problems of compliance mismatch. Although structure of blood vessels varies through a body, a "typical" artery 10, as shown in FIG. 1, includes three distinct layers, each performing specific basic functions. An intima 12, which includes an endothelium 14 attached to a basement membrane 16, provides a non-thrombogenic blood contacting surface. A media 18 contains smooth muscle cells (SMC's) 20 as well as elastin 22 and other intercellular connective and matrix materials, and supplies two other important properties to a blood vessel, namely compliance and contractility. In order to achieve these properties, tissues are oriented in a helical fashion in this medial layer 18. Another important property, namely structural integrity, is provided by an adventitia 24. A configuration of collagen fibers in the adventitia 24 provides for "stiffening" of the vessel when subjected to high internal pressures, i.e. a decrease in compliance with increased strain.

Figure 2:
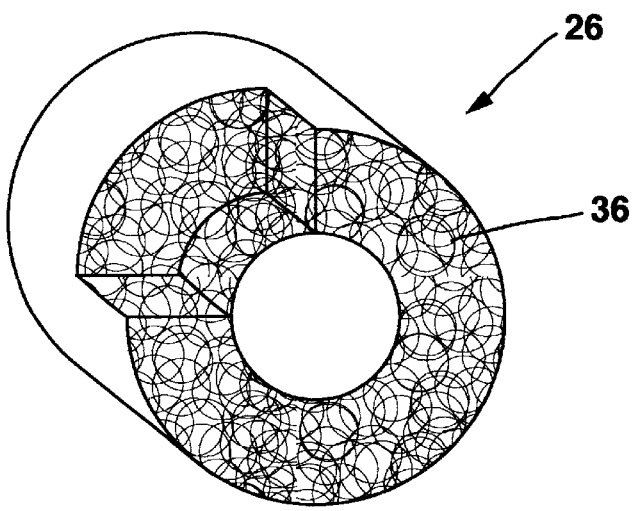
FIG. 2 is an enlargement of a cross-sectional view of a sliced section of a vascular graft made from prosthetic material having ingrowth matrices within interconnecting, spherical pores.
Figure 3:
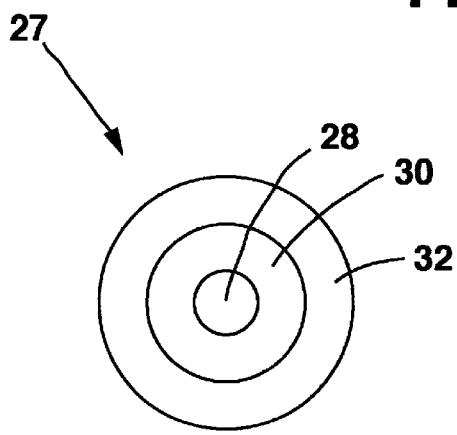
FIG. 3 is an enlarged cross-sectional view of a multilayer ingrowth matrix within one of the spherical pores in FIG. 2.

FIG. 2 shows a vascular graft 26 constructed from prosthetic material having a transmural scaffold with an ingrowth matrix 27 located within a network of spherical pores 36. The ingrowth matrix 27 in the prosthetic material of the invention, as shown in FIG. 3, preferably has at least three layers 28, 30 and 32. For example, an innermost layer 28 comprising polyethylene glycol can contain adhesive and degradation sites that allow for optimal ingrowth of endothelial cells. An intermediate layer 30 comprising polyethylene glycol can contain adhesive and degradation sites that allow for optimal ingrowth of smooth muscle cells. An outermost layer 32 can modify a surface of the scaffold material for macrophage pacification.

The layers 28, 30 and 32 can be constructed from either proteinaceous or synthetic materials, or a combination wherein at least one layer is constructed from a proteinaceous material and at least one layer is constructed from a synthetic material. The layers themselves can be constructed from all proteinaceous or all synthetic materials, or a combination of proteins and synthetic materials. Examples of suitable proteins include fibrin, collagen, and glycosaminoglycan. Examples of suitable synthetic materials include hydrogels, such as polyethylene glycol.

In terms of protein layers, a fibrin layer derivitized with peptides and/or growth factors is desirable because, for example, a fibrin matrix can allow introduction of active peptides into a factor XIII crosslinker of fibrinogen during fibrin polymerization. Since neurites and endothelial cells share laminin as a principle component of their basement membranes, and fibrin derivitized with laminin peptides is active in directing neurite extension, such derivitized matrices are potentially beneficial to transmural angiogenesis. Such fibrin matrices have binders which facilitate binding of heparin to heparin binding peptides, such as ATIII, and hence facilitate gradual release of growth factor from such matrices as ingrowing cells degrade the fibrin. Furthermore, each layer or concentration gradient of the matrix can comprise a different fibrin matrix derivitized with different peptides and/or growth factors. Suitable peptides include functional peptides of extracellular matrix molecules such as RGD (arginine-glycine-aspartic acid) or DGEA (aspartic acid-glycine-glutamic acid-alanine) from collagen, REDV (arginine-glutamic acid-aspartic acid-valine) or LDV (leucine-aspartic acid-valine) from fibronectin, SIKVAV (serine-isoleucine-lysine-valine-alanine-valine) or YIGSR (tyrosine-isoleucine-glycine-serine-arginine) from laminin. Suitable heparin binding growth factors include Vascular Endothelial Growth Factor (VEGF), beta Fibroblast Growth Factor (bFGF), and Platelet-Derived Growth Factor (PDGF).

A preferable synthetic layer is one constructed of polyethylene glycol. Polyethylene glycol is an ideal polymer to engineer because unmodified it does not mediate cellular adhesion. It can, therefore, be specifically modified to mediate adhesion of only specific cells. Combined with cell specific degradation sites, cell adhesive polyethylene glycol hydrogels can form an ingrowth layer. Like the fibrin layer, the polyethylene glycol layer can be derivitized with various peptides and/or growth factors.

Peptide derivitized polyethylene glycol hydrogels can be layered in the pores of a graft by (1) creating an innermost layer of polyethylene glycol containing adhesive and degradation sites that allow for optimal ingrowth of endothelial cells, (2) depositing a second layer of polyethylene glycol containing adhesive and degradation sites that allow for optimal ingrowth of smooth muscle cells, and (3) surface modifying the graft material for macrophage pacification.

Furthermore, a layer, either proteinaceous or synthetic, can also contain delivered genes, for example, antisense oligonucleotides towards angiogenic inhibitors such as thrombospondin 1 and 2, and pro-apoptotic factors such as the caspase family, Apaf-1. Another example includes genes for the increased expression of pro-angiogenic factors such as vascular endothelial growth factor, heme oxygenase-a, and anti-apoptotic factors such as Bcl-2 and Bcl-xL. Various constructs can be placed in suitable vectors. The constructs are either present in the matrix as DNA or enclosed in a suitable cationicliposome. Similar delivered genes can be incorporated in each layer, and can vary in concentration within each layer.

The multilayered ingrowth matrix should also contain a layered, degradable material in the channels 34 or pores 36 that allows for incorporation of adhesive peptide sequences for cell infiltration and migration, enzymatically degradable peptide sequences, and optional cytokines in the matrix. All of these substances encourage differential cell ingrowth. Suitable layered materials include both proteins and synthetic materials. Examples of suitable proteins include fibrin, collagen, and glycosaminoglycan. Examples of suitable synthetic materials include hydrogels, such as polyethylene glycol. These materials are arranged in two to eight layers, thereby forming the ingrowth matrix. For example, the ingrowth matrix can have an outermost layer 32 including a collagen layer that has been heparinized, and a drug release layer, and up to five various ingrowth layers.

Figure 4:
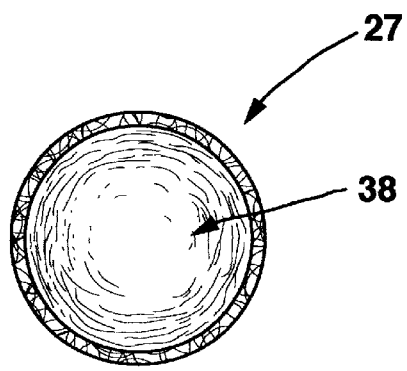
FIG. 4 is an enlarged cross-sectional view of an ingrowth matrix having a concentration gradient within one of the spherical pores in FIG. 2.

In an alternate embodiment, shown in FIG. 4, a concentration gradient 38 replaces the distinct layers 28, 30 and 32 of the ingrowth matrix 27. More specifically, one material is present throughout the ingrowth matrix 27, but in various concentrations between a core of the ingrowth matrix 27 and an outermost surface of the ingrowth matrix 27. Like the layers 28, 30 and 32 in the multilayered embodiment, the concentration gradient 38 is present throughout the transmural ingrowth channels 34 and/or pores 36. Furthermore, varying concentrations within the ingrowth matrix 27 are designed to perform specific functions. For example, different cells can be sensitive to different concentrations, therefore a concentration gradient allows multiple ingrowth options within one matrix 27. In yet a further embodiment, a concentration gradient can be present within individual layers of the ingrowth matrix 27. More specifically, one material is present throughout an individual layer, but the material can vary in concentration throughout that layer.

Figure 5:
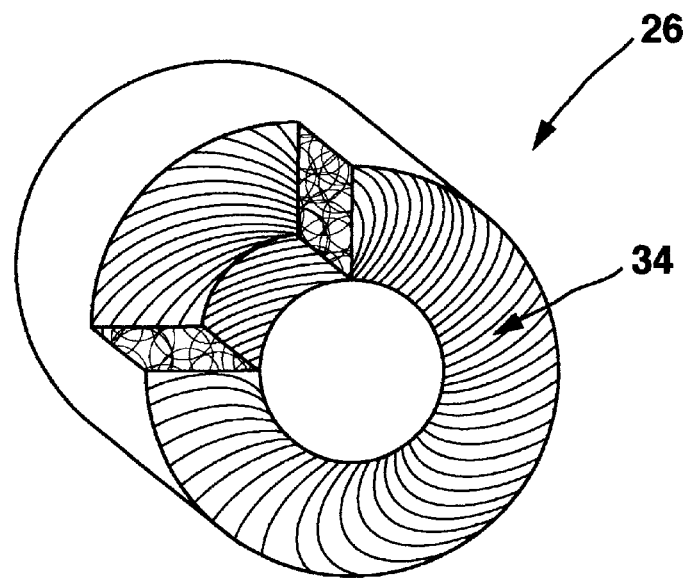
FIG. 5 is an enlargement of a cross-sectional view of a sliced section of a vascular graft made from prosthetic material having ingrowth matrices within interconnecting, helically oriented channels.
Figure 6:
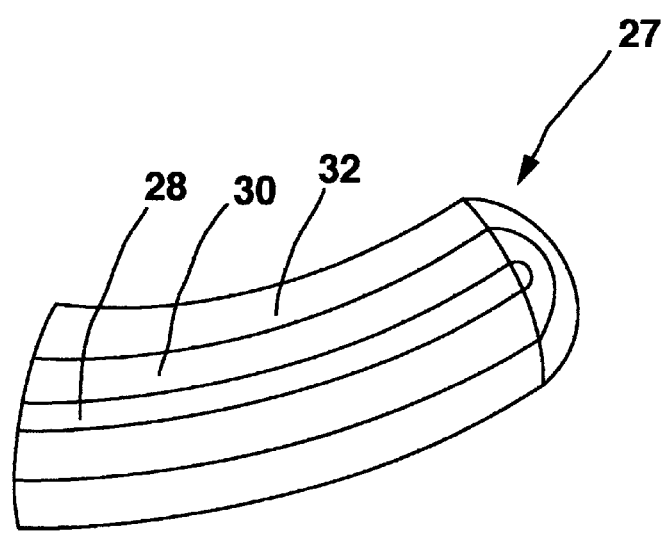
FIG. 6 is an enlarged cross-sectional view of a multilayer ingrowth matrix within one of the channels in FIG. 5.

The multilayer ingrowth matrix can be located in a scaffold of interconnecting, helically oriented channels 34, and/or interconnecting, uniformly shaped pores 36. FIG. 5 shows a vascular graft 26 constructed from prosthetic material having a transmural scaffold with an ingrowth matrix 27 located within a network of interconnected, helically oriented channels 34. FIG. 6 shows the multilayer ingrowth matrix 27 as it appears in one of the channels 34 in the graft 26 of FIG. 5.

The channels 34 are well-defined, such that all, or substantially all, of the channels have diameters within a range of about 20 µm of one another, more preferably within a range of about 10 µm of one another. The channel diameters should be in a range of 10 to 300 µm, more preferably 40 to 110 µm. Similarly, the pores 36, which are preferably spherical, are well-defined with all, or substantially all, of the pores having diameters within a range of about 20 µm of one another, more preferably within a range of about 10 µm of one another. The diameters of the pores 36 should be in a range of 10 to 300 µm, more preferably 40 to 110 µm.

In a graft 26 having interconnecting, helically oriented channels 34, in order to encourage tissue ingrowth, the channels 34 should be oriented in such a way as to correspond to the helical arrangement of vascular tissues in the walls of natural arteries. The graft structure thereby creates an optimal strain environment that facilitates and encourages the development and maintenance of endothelial and smooth muscle cells in the vessel. By getting the smooth muscle cells to grow helically on the graft 26 along the spiral channels 34, the graft 26 acquires radial compliance and behaves like a real blood vessel. To achieve high porosity, the channels 34 should be arranged at a very narrow angle, for example a 200 µm pitch. "Pitch" is the length, measured along the axis, of a complete rotation of a given channel about the circumference of the graft 26. For larger angles, a 10 mm pitch is suitable. The pitch can be varied through the thickness of the wall by increasing or decreasing the pitch at a predefined rate as one builds up the graft wall, or alternating between two or more pitches in alternate layers.

Because of complex interaction between inflammatory mediators and connective tissue cells, healing of a vascular prosthesis is best achieved in the absence of ongoing chronic foreign body reactions. In order to minimize foreign body reaction and to encourage differential cell ingrowth, the channels and/or pores of the graft 26 can be lined with a biocompatible substance, such as a hydrogel, that does not adhere to, and is not degraded by macrophages. In a preferred embodiment, the outermost layer 32 of the ingrowth matrix is a surface coating that substantially lines an inner surface of the channels and/or pores. Like the other layers, the surface coating can be either proteinaceous or synthetic, or a combination thereof. For example, the surface coating can be a covalent hydrogel surface modification of polyethylene glycol. The surface coating is designed for macrophage pacification to protect the interior of the graft from ongoing chronic foreign body reaction.

Ideally, the prosthetic material should provide high porosity for maximal cell ingrowth and minimal bulk compressibility (to allow for compressibility associated with contractility). The resulting graft should have structural integrity and viscoelastic properties similar to those observed for natural vessels. Furthermore, in order to minimize foreign body reaction and to encourage differential cell ingrowth, the graft should also exhibit long-term in-vivo stability. The porosity should be oriented in such a way as to obtain circumferential and longitudinal orientation from radial ingrowth to allow physiological contractility. Furthermore, the graft must have structural integrity and viscoelastic properties similar to those observed for natural vessels.

The graft is well-suited for small diameter vascular grafts, as well as larger diameter vascular grafts. The graft is preferably a tubular structure having an internal diameter in a range of 1–20 mm, preferably in a range of 2–6 mm. The walls of the graft can vary in thickness from about 0.1 to about 5 mm, more preferably from 0.4 to 1.5 mm, depending on the diameter of the graft. The thickness of individual layers of the ingrowth matrix can vary from about 10 to about 100 microns for the ingrowth layers 28 and 30 and the outermost surface modifying layer 32, more preferably from about 10 to about 30 microns.

The porous scaffold of the present invention can be made using a variety of techniques. The most preferred method for producing a graft having spherical pores is a vacuum impregnation technique. In this method, a casting device having a mandrel, a top manifold and a bottom manifold is used to produce the graft. The top manifold allows for application of air pressure to a top portion of a mold or molds. The bottom manifold allows for application of a vacuum to a bottom portion of the mold or molds. The molds are cylindrical tubes with an inside diameter corresponding to a desired outside diameter of a resulting graft. The molds are used in conjunction with cylindrical central rods having an outside diameter corresponding to a desired inner diameter of the resulting graft.

Once the casting device is assembled, the grafts are formed by filling an annular space between the central rod and the tube with an extractable filler. Suitable filler materials include alginate, gelatin, carbohydrates, inorganic and organic salts. A reservoir is filled with a graft material solution comprising graft material in a graft material solvent.

The term "graft material" means any polymeric or other material that can be dissolved in a suitable solvent and re-solidified after graft manufacture by air-drying, phase inversion, or combinations thereof. Examples of suitable graft materials include: thermoplastic elastomers including thermoplastic polyurethanes, e.g. Pellethane, Biomer type polyurethanes, Chronoflex, and Hydrothane. In particular, a polyurethane developed by Medtronic and described in U.S. Pat. No. 4,873,308 is an example of a suitable graft material.

The term "graft material solvent" means any solvent capable of dissolving the graft material. Examples of suitable solvents include: N-methyl pyrrolidone (NMP) and 1-methyl-2-pyrrolidinone.

The term "graft material solution" means a solution of the graft material in the graft material solvent in concentrations ranging from 1 to 40% by mass, more typically 5 to 30% by mass, usually 10 to 25% by mass.

Once the reservoir is filled with graft material solution, the top manifold is then closed and pressure is applied to the top manifold and/or vacuum is applied to the bottom manifold to force the graft material solution into interstices between the packed extractable filler.

After the graft material solution is forced into the interstices, the tube, graft and rod are removed from the device. Precipitation of the graft (defined as removal of the graft material solvent) is begun with immersion into precipitation solvent. The central rod is then removed from the graft and the tube. Precipitation of the graft material and extraction of the graft material solvent are completed by extended immersion in the precipitation solvent. The precipitated graft is removed from the tube. The extractable filler is extracted from the precipitated graft material to produce the porous structure of the invention. The filler can be extracted using a filler extraction solvent, such as water.

Other methods for producing grafts with spherical pores include a paste molding technique, wherein a paste prepared from an extractable filler and a graft material solution is rolled onto a mandrel, and the graft material solution is subsequently precipitated and the filler is extracted, as in the vacuum impregnation technique. A paste extrusion technique is similar to the paste molding technique but instead of rolling the paste onto a mandrel, the paste is extruded through an annular orifice. A dip coating technique is also very similar to the paste molding technique, but instead of rolling the paste onto a mandrel, the paste is deposited in consecutive layers onto a mandrel. A melt extrusion technique is another method for producing a layer having spherical pores. In the melt extrusion method, a thermoplastic elastomer is extruded with the use of physical and/or chemical blowing agents to produce a foamed graft. The foamed graft is then annealed and reticulated, where needed, to effect an open-cell structure.

The most preferred method for producing a graft with helically oriented, interconnected transmural ingrowth channels is a fiber winding and extraction technique. This method involves assembling a mandrel in a custom-designed winding device. The device can be as simple as a personal computer attached to a controller which is further attached to two motors. One motor drives translational movement of the fiber, while the other motor drives rotation of the mandrel. The device allows for accurate control over winding speed and position of the rotating mandrel and translational movement of the fiber, thereby allowing for the accurate placement of wound fibers on the mandrel.

Once the winding device is assembled, an extractable fiber is coated with a solution containing a biocompatible material. The extractable fiber is made of alginate, gelatin, carbohydrates, inorganic or organic salts, for example. The coating solution includes the aforementioned graft material dissolved in a suitable graft material solvent. After the fiber is coated, the fiber is wound onto the mandrel. The coating solution is then solidified by phase precipitation, wherein the graft is immersed into a precipitation solvent, and/or by drying. The extractable fiber is extracted by applying a fiber extraction solvent to produce channels in the space occupied by the fiber.

Other methods for producing layers with helically oriented, interconnected transmural ingrowth channels include a melt extrusion technique with oriented fibers, wherein a molten graft material containing chopped strands of extractable fibers is extruded from an extrusion die specially adapted to orient fibrous fillers in an extrudate. Physical and/or chemical blowing agents can be used to produce a foamed graft.

Another method for producing a graft with channels is a particle and fiber extraction technique using a layered method, wherein a paste is prepared from a graft material solution and an extractable filler, and a layer of the paste is deposited and pressed onto a mandrel. An extractable fiber is wound onto the paste layer. Additional, alternating layers of paste and extractable fiber can be deposited on the mandrel. The graft material solution is then precipitated by phase precipitation and/or by drying. The extractable fiber and extractable filler are extracted, either simultaneously or consecutively, by applying a fiber extraction solvent to produce channels in the space occupied by the extractable fiber. A filler extraction solvent can be the same solvent as the fiber extraction solvent, and may vary only in temperature.

A further method for producing layers with channels is a particle and fiber extraction technique using a continuous method, which is like the layered method but in the continuous method the paste is deposited onto the mandrel simultaneously while the extractable fiber is wound onto the mandrel.

The above-described prosthetic material can also be used in other items, such as a sewing ring or a synthetic heart valve.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A prosthetic material comprising:
   a scaffold having interconnecting, helically oriented channels; and
   an ingrowth matrix within said helically oriented channels, wherein the ingrowth matrix comprises a concentration gradient of material.

2. The prosthetic material of claim 1 wherein the material in the concentration gradient comprises a synthetic material.

3. The prosthetic material of claim 2 wherein the synthetic material comprises a hydrogel.

4. The prosthetic material of claim 1 wherein the material in the concentration gradient comprises a protein.

5. The prosthetic material of claim 4 wherein the protein is selected from the group consisting of fibrin, collagen, glycosaminoglycan, and combinations thereof.

6. The prosthetic material of claim 1 wherein the material in the concentration gradient comprises a protein and a synthetic material.

7. The prosthetic material of claim 1 wherein the material in the concentration gradient comprises a growth factor.

8. The prosthetic material of claim 1 wherein the material in the concentration gradient comprises a peptide.

9. The prosthetic material of claim 1 wherein the concentration gradient comprises a delivered gene.

10. The prosthetic material of claim 1 wherein the concentration gradient comprises a fibrin matrix.

11. The prosthetic material of claim 1 wherein the concentration gradient comprises a polyethylene glycol matrix.

12. The prosthetic material of claim 1 wherein substantially all of the channels have diameters within 300 $\mu$m of one another.

13. The prosthetic material of claim 1 comprising a vascular graft.

14. The prosthetic material of claim 1 comprising a sewing ring.

15. The prosthetic material of claim 1 comprising a synthetic heart valve.

* * * * *